United States Patent
Amurthur

(10) Patent No.: US 10,926,089 B2
(45) Date of Patent: Feb. 23, 2021

(54) STIMULATION METHODS AND APPARATUS

(71) Applicant: Jiva Medical Systems, Inc., Los Gatos, CA (US)

(72) Inventor: Badri Amurthur, Los Gatos, CA (US)

(73) Assignee: Jiva Medical Systems, Inc., Los Gatos, CA (US)

( * ) Notice: Subject to any disclaimer, the term of this patent is extended or adjusted under 35 U.S.C. 154(b) by 0 days.

(21) Appl. No.: 16/723,749

(22) Filed: Dec. 20, 2019

(65) Prior Publication Data

US 2020/0139124 A1 May 7, 2020

Related U.S. Application Data

(63) Continuation of application No. PCT/US2018/031199, filed on May 4, 2018.
(Continued)

(51) Int. Cl.
*A61N 1/36* (2006.01)
*A61B 5/01* (2006.01)
*A61B 5/024* (2006.01)

(52) U.S. Cl.
CPC ............ *A61N 1/36038* (2017.08); *A61B 5/01* (2013.01); *A61B 5/024* (2013.01); *A61B 2562/0219* (2013.01); *A61N 1/36082* (2013.01)

(58) Field of Classification Search
CPC .. A61N 1/36038; A61N 1/36082; A61B 5/01; A61B 5/024; A61B 2562/0219
See application file for complete search history.

(56) References Cited

U.S. PATENT DOCUMENTS 5,788,656 A 8/1998 Mino et al.
7,840,278 B1 11/2010 Puskas et al.
(Continued)

FOREIGN PATENT DOCUMENTS

DE 102010021540 A1 11/2011
DE 102011119436 A1 5/2013
(Continued)

OTHER PUBLICATIONS

Akerman, et al. Pearls and pitfalls in experimental in vivo models of migraine: dural trigeminovascular nociception. Cephalalgia 33.8 (2013): 577-592.
(Continued)

*Primary Examiner* — Rex R Holmes
(74) *Attorney, Agent, or Firm* — Wilson Sonsini Goodrich and Rosati, P.C.

(57) ABSTRACT

The present methods and apparatus can provide improved efficacy with improved tolerance. The methods and apparatus can be configured to alter the stimulus, which can decrease neural adaptation of the subject and provide an improved response. The acoustic stimulus can be delivered as a tone, which can make the stimulus more acceptable to the subject receiving the stimulus. The stimulus may comprise a varying stimulus in order to decrease neural adaptation to the stimulus. The stimulus can be varied by varying one or more of a duty cycle, a frequency, or a shape of the waveform. The waveform may comprise a plurality of individual pulses, in which the waveform varies among pulses of the plurality. Acoustic stimulation can be combined with electrical stimulation. The device may comprise a plurality of sensors to determine the response of the subject.

36 Claims, 11 Drawing Sheets

Related U.S. Application Data

(60) Provisional application No. 62/502,256, filed on May 5, 2017.

(56) References Cited

U.S. PATENT DOCUMENTS

| | | | |
|---|---|---|---|
| 8,142,373 B1 | 3/2012 | Riles et al. | |
| 1,004,590 A1 | 8/2018 | Harper et al. | |
| 2003/0195588 A1* | 10/2003 | Fischell | A61N 2/02 607/55 |
| 2007/0106344 A1 | 5/2007 | Darley et al. | |
| 2007/0232962 A1 | 10/2007 | Zumeris et al. | |
| 2007/0250145 A1 | 10/2007 | Kraus et al. | |
| 2008/0004672 A1 | 1/2008 | Dalal et al. | |
| 2008/0249439 A1 | 10/2008 | Tracey et al. | |
| 2008/0288016 A1 | 11/2008 | Amurthur et al. | |
| 2010/0198282 A1 | 8/2010 | Rogers et al. | |
| 2010/0282070 A1 | 11/2010 | Ishikawa et al. | |
| 2011/0066176 A1 | 3/2011 | Coole et al. | |
| 2013/0142378 A1 | 6/2013 | Bravo et al. | |
| 2013/0282070 A1 | 10/2013 | Cowan et al. | |
| 2013/0303953 A1 | 11/2013 | Lattner et al. | |
| 2014/0180181 A1 | 6/2014 | Von Oepen et al. | |
| 2015/0141879 A1 | 5/2015 | Harper et al. | |
| 2015/0360030 A1* | 12/2015 | Cartledge | A61N 1/0456 607/60 |

FOREIGN PATENT DOCUMENTS

| | | |
|---|---|---|
| DE | 102012005513 A1 | 9/2013 |
| JP | H09108355 A | 4/1997 |
| JP | 2009022699 A | 2/2009 |
| WO | WO-2009106255 A1 | 9/2009 |
| WO | WO-2012094484 A1 | 7/2012 |
| WO | WO-2018204853 A1 | 11/2018 |

OTHER PUBLICATIONS

Dasilva, et al. tDCS-induced analgesia and electrical fields in pain-related neural networks in chronic migraine. Headache: The Journal of Head and Face Pain 52.8 (2012): 1283-1295.

Hu, et al. Burden of migraine in the United States: disability and economic costs. Archives of internal medicine 159.8 (1999): 813-818.

Jannetta. Neurovascular compression in cranial nerve and systemic disease. Annals of surgery 192.4 (1980): 518.

Meng, et al. Migraine prevention with a supraorbital transcutaneous stimulator: a randomized controlled trial. Neurology 81.12 (2013): 1102-1103.

Mosqueira, et al. Vagus nerve stimulation in patients with migraine. Revista de neurologia 57.2 (2013): 57-63.

Olesen, et al. Emerging migraine treatments and drug targets. Trends in pharmacological Sciences 32.6 (2011): 352-359.

Pedersen, et al. Neurostimulation in cluster headache: a review of current progress. Cephalalgia 33.14 (2013): 1179-1193.

Salvador; Quiroz-Gonzalez et al., "Acupuncture Points and Their Relationship with Multireceptive Fields of Neurons", JAMS, 2017, 10(2), 81-89.

Schoenen, et al. Migraine prevention with a supraorbital transcutaneous stimulator A randomized controlled trial. Neurology 80.8 (2013): 697-704.

Silberstein, et al. Botulinum toxin type A as a migraine preventive treatment. Headache: The Journal of Head and Face Pain 40.6 (2000): 445-450.

* cited by examiner

STIMULATION METHODS AND APPARATUS

CROSS-REFERENCE

The present application is a continuation of PCT Application No. PCT/US18/31199, filed May 4, 2018; which claims priority to U.S. Provisional Patent Application No. 62/502,256, filed May 5, 2017; the entire disclosures of which are incorporated herein by reference.

BACKGROUND OF THE INVENTION

Prior methods and apparatus for providing auricular nerve stimulation to patients can be less than ideal in at least some instances. Although vibratory approaches have been proposed, such neural stimulation may not be well tolerated by users in at least some instances, which can lead to less than ideal compliance and therapeutic outcomes. Also, the prior approaches can be less than ideally suited to determine the treatment parameters used to treat a subject such as a human patient. Also, work in relation to the present disclosure suggests that the neural system can adapt to a stimulus, and the prior methods and apparatus can be less than ideally suited to address neural adaptation which may decrease the efficacy of treatment.

SUMMARY OF THE INVENTION

The present methods and apparatus can provide improved efficacy with improved tolerance and reduced undesirable device-related effects. The apparatus may be non-invasive such as a wearable device. The methods and apparatus can be configured to alter the stimulus, which can decrease neural adaptation of the subject and provide an improved response. The present apparatus and method can be placed to various locations of body for vibratory stimulation of underlying nerve structures. The various locations may be determined according to a specific therapy or medication. For example, the locations may comprise locations corresponding to Chinese acupuncture points according to Traditional Chinese Medicine such as a limb and various other peripheral locations. In another example, the apparatus is placed near an auricular location. For auricular applications, the vibratory stimulus can be delivered in ways that coincide with certain perceptions of pitch and pleasing, consonant combinations of pitch, which can make the stimulus more acceptable to the subject receiving the stimulus. The stimulus may comprise a varying stimulus in order to decrease neural adaptation to the stimulus. The stimulus can be varied by varying one or more of a duty cycle, a frequency, amplitude, a shape of the waveform, or a combination of any of the above. The waveform may comprise a plurality of individual vibratory pulses, in which the waveform varies among pulses of the plurality. Mechanical vibratory stimulation can be combined with electrical stimulation, such that targeted nerves are treated with both vibratory and mechanical stimulation. The device may comprise a plurality of sensors to determine the response of the subject, and feedback from the sensors can be used to adjust the treatment.

In one aspect of the invention, an apparatus to treat a subject is provided. The apparatus comprises: an actuator to provide a vibratory stimulus and acoustic stimulus to the skin of the subject in an area underlying sensory nerve fibers and subcutaneous tissues, and a processor coupled to the actuator, the processor configured with instructions to vibrate the skin and underlying subcutaneous tissues and nerve structures of the subject.

In some embodiments, the processor is configured with instructions to deliver a plurality of vibratory pulses to the subject, the plurality of pulses comprising a frequency corresponding to a harmonic of a pitch. In some cases, the frequency is within a range from about 20 Hz Hertz to about 20,000 Hertz.

In some embodiments, the processor is configured with instructions to automatically deliver the vibratory stimulus and acoustic stimulus based on real-time sensor measurements. In some embodiments, the apparatus further comprises stimulation electrodes to deliver an electrical stimulus to the subject. In some embodiments, the apparatus further comprises stimulation electrodes to deliver an electrical stimulus to the skin of the subject in an area comprising underlying sensory nerve fibers and subcutaneous tissues and optionally wherein the actuator is located in proximity to the electrodes in order to stimulate the area with mechanical vibration and electrical stimulation. In some embodiments, the apparatus further comprises drug delivery mechanism configured to release drug in combination with the vibratory stimulus and acoustic stimulus.

In another aspect, a non-transitory computer-readable medium comprising machine executable code that, upon execution by one or more processors, implements a method for treating a subject is provided. The method comprises: positioning an actuator to provide a vibratory stimulus and acoustic stimulus to the skin of the subject in an area underlying sensory nerve fibers and subcutaneous tissues; and generating instructions to the actuator to vibrate the skin and underlying subcutaneous tissues and nerve structures of the subject.

In some embodiments, the instructions comprise delivering a plurality of vibratory pulses to the subject, the plurality of pulses comprising a frequency corresponding to a harmonic of a pitch. In some cases, the frequency is within a range from about 20 Hz Hertz to about 20,000 Hertz. In some cases, the one or more processors are configured to stimulate the ear with a plurality of frequencies corresponding to frequencies of pitch.

In some embodiments, the instructions are generated based at least in part on real-time sensor measurements. In some embodiments, the method further comprises delivering an electrical stimulus to the subject using stimulation electrodes. In some embodiments, the method further comprises delivering an electrical stimulus to the skin of the subject in an area comprising underlying sensory nerve fibers and subcutaneous tissues using stimulation electrodes and optionally wherein the actuator is located in proximity to the electrodes in order to stimulate the area with mechanical vibration and electrical stimulation. In some embodiments, the method further comprises delivering drug in combination with the vibratory stimulus and acoustic stimulus.

In a related yet separate aspect, a method for treating a subject is provided. The method comprises: positioning an actuator to provide a vibratory stimulus and acoustic stimulus to the skin of the subject in an area underlying sensory nerve fibers and subcutaneous tissues; and generating, with aid of one or more processors, instructions to the actuator to vibrate the skin and underlying subcutaneous tissues and nerve structures of the subject.

In some embodiments, the instructions comprise delivering a plurality of vibratory pulses to the subject, the plurality of pulses comprising a frequency corresponding to a harmonic of a pitch. In some cases, the frequency is within a range from about 20 Hz Hertz to about 20,000 Hertz. In some cases, the one or more processors are configured to stimulate the ear with a plurality of frequencies corresponding to frequencies of pitch.

In some embodiments, the instructions are generated based at least in part on real-time sensor measurements. In some embodiments, the method further comprises delivering an electrical stimulus to the subject using stimulation electrodes. In some embodiments, the method further comprises delivering an electrical stimulus to the skin of the subject in an area comprising underlying sensory nerve fibers and subcutaneous tissues using stimulation electrodes and optionally wherein the actuator is located in proximity to the electrodes in order to stimulate the area with mechanical vibration and electrical stimulation. In some embodiments, the method further comprises delivering drug in combination with the vibratory stimulus and acoustic stimulus.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The presently disclosed methods and apparatus can be configured in many ways and are well suited for combination with many types of therapy. For example, the presently disclosed methods and apparatus can be combined with prior defibrillators to provide an improved therapeutic benefit. The methods and apparatus disclosed herein are well suited for combination with remote cloud based servers and analytics, which can be used to transmit therapy to the subject. Although reference is made to therapy, the device can be configured to provide many additional or alternative benefits to the user, such as stimulation or relaxation, for example.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is used inclusively.

The apparatus can be applied to various locations on a body in a non-invasive manner, for example. In some instances, the various locations may be selected according to the locations of peripheral nerves. A geometry or form factor of the apparatus may vary based on the different locations it is placed onto. For instance, the apparatus worn around a wrist or arm may have a different dimension or geometry from the one worn around ears. However, it should be appreciated that the method providing the stimulation or function can be substantially the same across apparatuses placed on different locations. Different treatment tables comprising parameters corresponding to the apparatuses placed on different locations may be provided. In some embodiments, the apparatus may be placed around an auricular location.

FIGS. 1-3B show known ear anatomy and pathways suitable for incorporation in accordance with embodiments disclosed herein, and are described in U.S. Pat. Pub. No. US2015/0141879, entitled "Device, System and Method for Reducing Headache Pain", by Harper and Sauerland.

Figure 1:
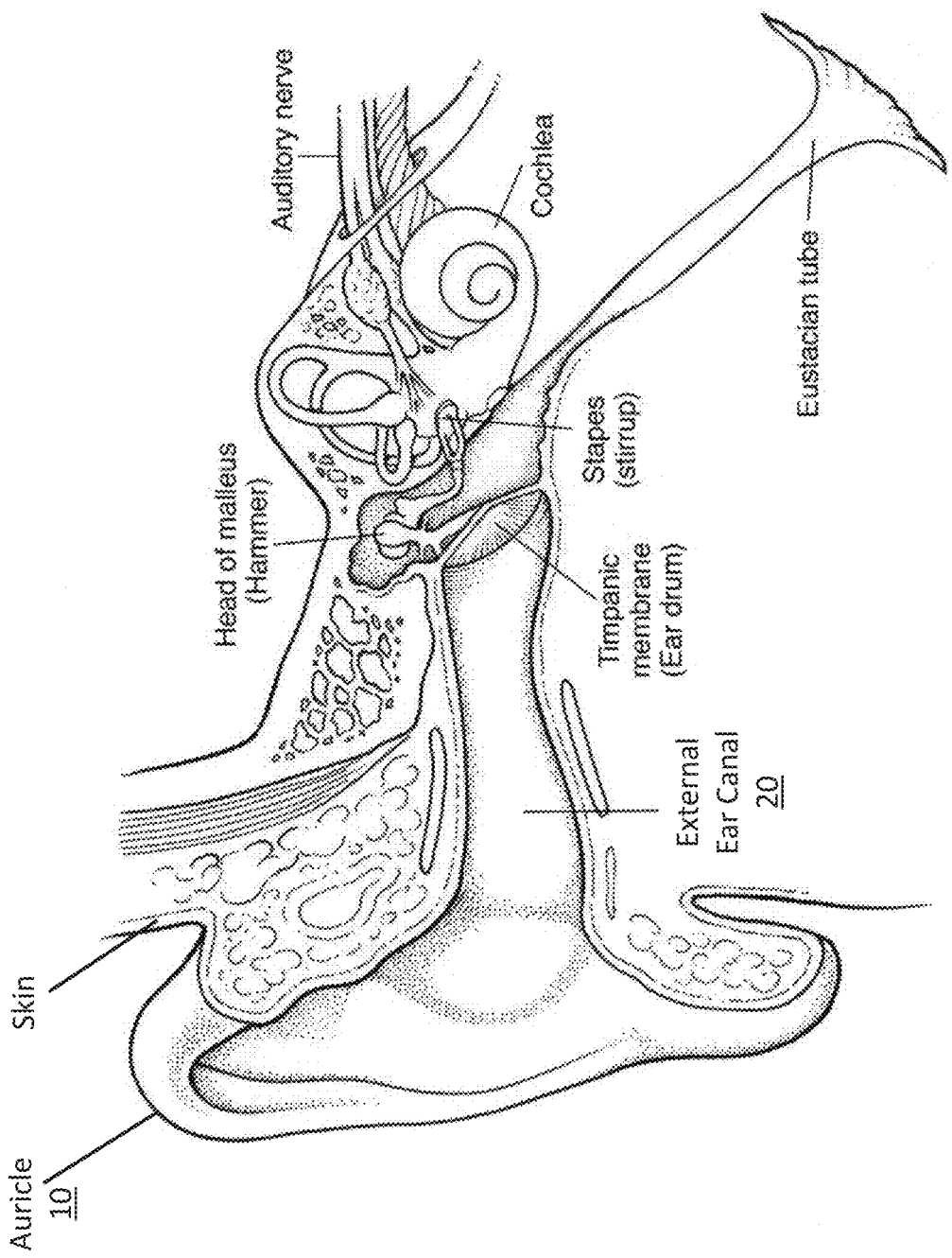
FIG. 1 is a cross-sectional view through the external ear canal and auricle, suitable for combination in accordance with some embodiments.

FIG. 1 is a cross-sectional view through the external ear canal 20 and auricle 10, showing the structures affected. The provided device comprises a portion to contact at least a portion of the external ear canal 20 and/or the auricle 10.

Figure 2B:
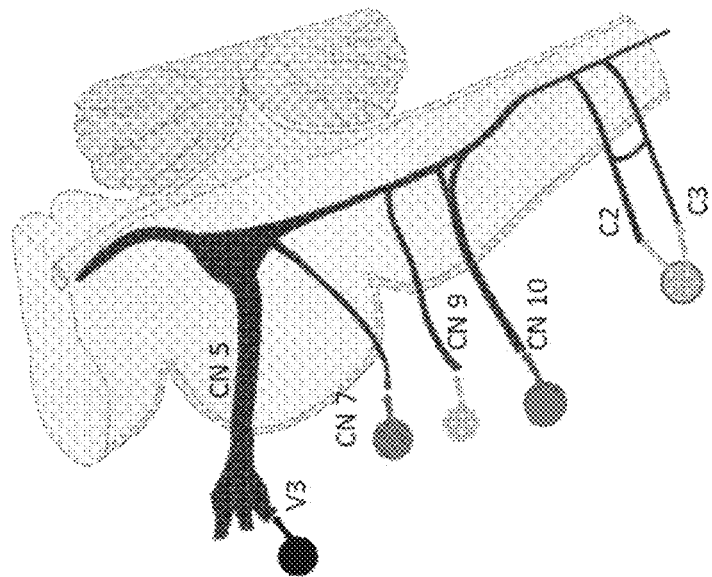
FIG. 2B is an illustration of the brain stem nuclei involved in sensory information processing of the trigeminal nerve, suitable for combination in accordance with some embodiments.
Figure 2A:
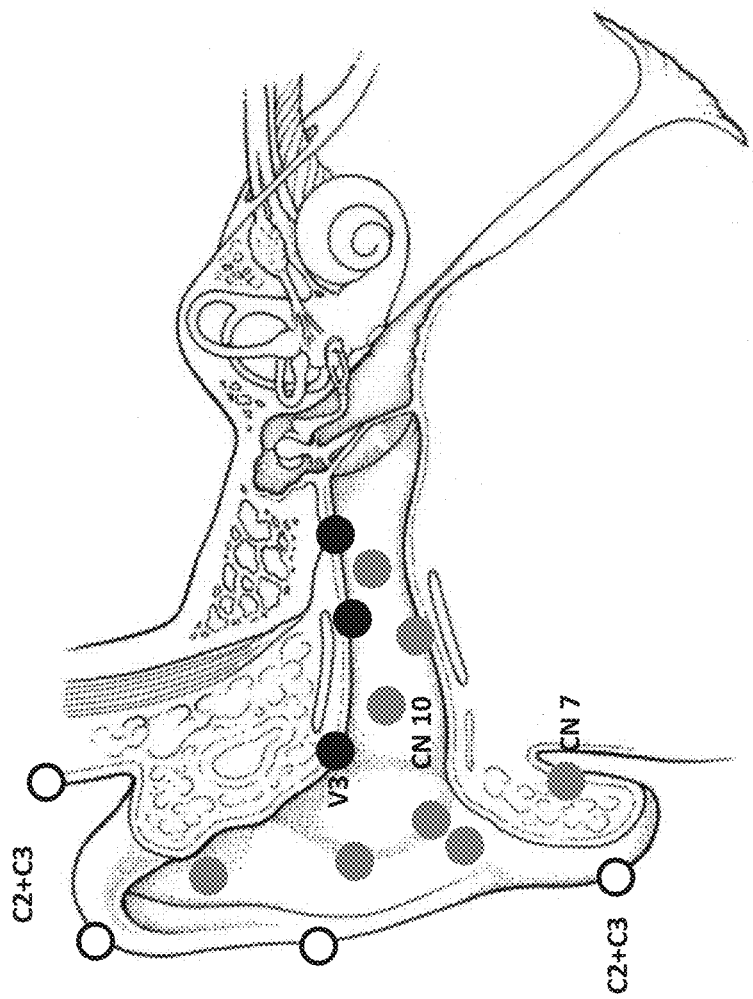
FIG. 2A is an illustration of sensory input from the ear concha and the external ear canal to spinal nerves C2, and C3, and cranial nerves 5, 7, 9 and 10, suitable for combination in accordance with some embodiments.

FIG. 2A is an illustration of sensory input from the ear concha and the external ear canal to spinal nerves C2, and C3, and cranial nerves 5, 7, 9 and 10. The external ear canal (external acoustic meatus) is mainly supplied by the third division of cranial nerve 5, cranial nerves 10 and 9; the last serves the area of the tympanic membrane. Vibratory stimuli are transferred from the external ear canal to the tympanic membrane.

FIG. 2B is an illustration of the brain stem nuclei involved in sensory information processing of the trigeminal nerve. The principal, or main sensory nucleus of cranial nerve 5 mediates touch, vibration, and pressure, but pain is mediated by the descending or spinal nucleus of 5, which is contiguous with the spinal tract mediating pain from lower nerves. FIG. 2A and FIG. 2B illustrate how pain mediated by cranial nerves 7, 9, 10 and spinal nerves C2 and C3 use the same descending spinal nucleus and spinal tract.

Figures 3A, 3B:
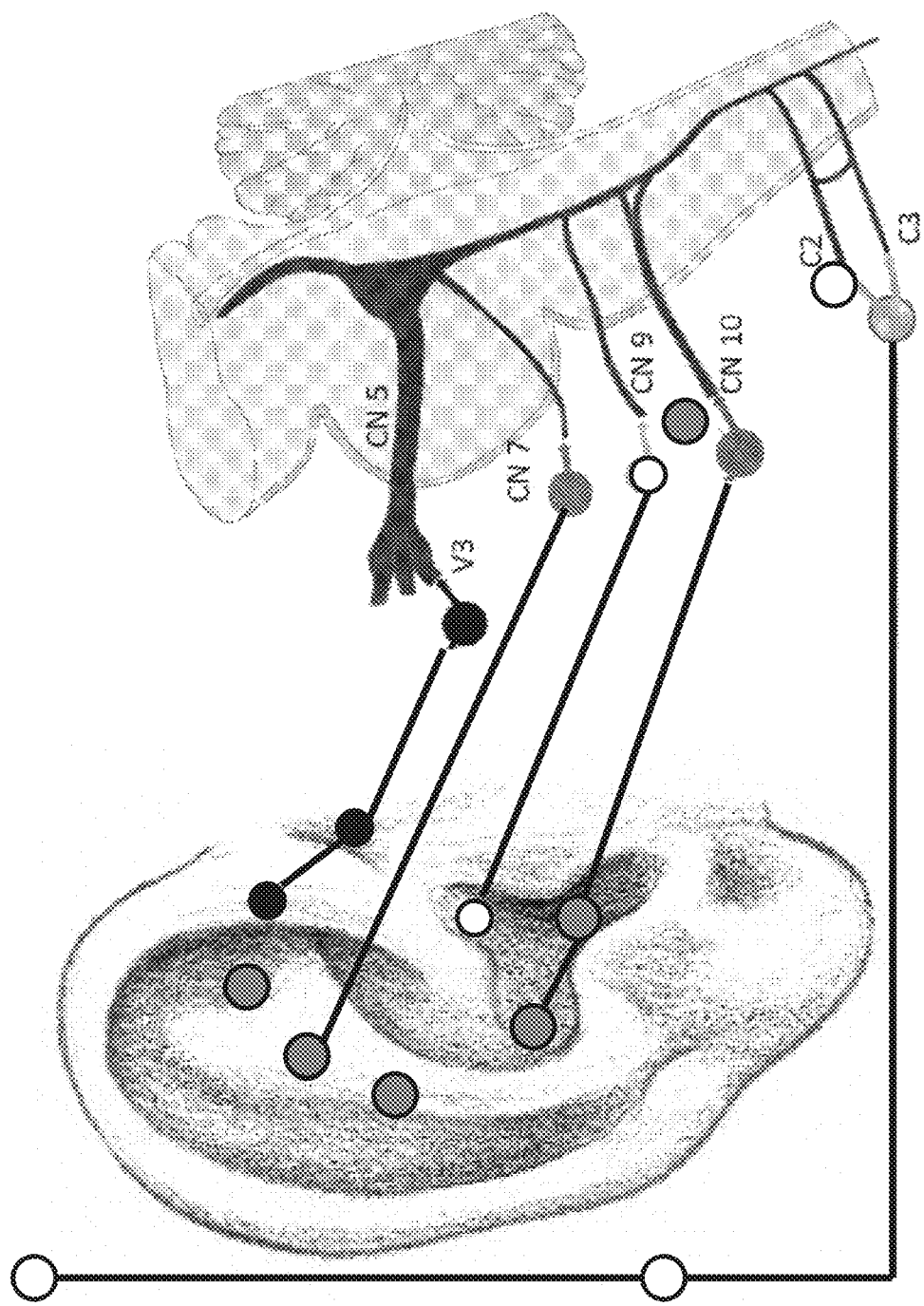
FIG. 3A illustrates sensory input from the ear auricle, concha and the external ear canal to C2, C3, and cranial nerves 5, 7, 9 and 10, suitable for combination in accordance with some embodiments.
FIG. 3B illustrates brain stem nuclei as similarly depicted in FIG. 2B, suitable for combination in accordance with some embodiments.

FIGS. 3A and 3B illustrate sensory input from the ear auricle, concha and the external ear canal to C2, C3, and cranial nerves 5, 7, 9 and 10. The external ear canal (external acoustic meatus) is mainly supplied by cranial nerve 5 (V3), 7, and 10, and spinal nerves C2 and C3 contribute to the innervation of the auricle. Cranial nerve 9 supplies the area of the tympanic membrane. Vibratory stimuli from the external ear canal are transferred to the tympanic membrane. The device or apparatus as described herein may be configured to stimulate some or all of the spinal nerves or cranial nerves as illustrated in the figures.

TABLE 1

Therapy and Device Combinations

| DEVICE | RESPONSIVE Tx | EASE OF USE | CONNECTIVITY |
|---|---|---|---|
| Form Factor Vibratory and Acoustic Electrical Combination Stimulation Modes | Sensors | Multi-frequency pitch | Wireless |
| Unilateral Bi Lateral Synchronized Stimulus Location | Smart Dosing | Noise Cancellation Audible/ Non-Audible | App on Watch/Phone |
| Auricular Locations overlying Peripheral nerves Stimulus Delivery | Intelligent-Titration | App Driven | Cloud Based Platform |
| Waveform pattern Pulse width, frequency, amplitude, duty cycle ON/Off Switch | AF, Brady, Tachy etc | User Report | Remote Access |

| DOSING | PHYSIOMETRY | INDICATIONS | COMBINATION Tx |
|---|---|---|---|
| Parameters - Range Stimulus Pattern | HR, HRV Sleep Quality | Pain Myocardial Infarction (MI) | Multi-Modal Stim Auricular Stim with wearable defibrillator |
| Titration | O₂ Saturation | Stroke | AS with implantable ECG AS with Drugs |
| Fulcrum (functional effects of efferent reflex) | Breathing | Inflammation Heart failure Atherosclerosis | AS with Drug Patches (such as Scapalomine) |

Table 1 shows attributes of the methods and apparatus disclosed herein in accordance with some embodiments. The user device may comprise a user wearable device that is configured to fit on the ear of the human subject with a suitable form factor for comfort. Alternatively or in combination, the user device may comprise a suitable form factor to be fit with other locations of human subject (e.g., limbs). For instance, the user device may have a form factor such as a wrist band, arm band/patches to be placed to locations other than the auricular location. The device can be configured to provide a combination of mechanical vibration and electrical stimulation to the skin. The device can be configured to provide a combination of vibratory stimulus and acoustic stimulus. The device typically comprises an acoustic vibratory actuator and may include one or more electrodes for combination therapies. In some cases, the device may further comprise drug delivery features. Alternatively, the device may be operably coupled to a drug delivery component such as an electronically controlled drug releasing skin patch or implantable drug delivery component to deliver pre-programmed drug infusion to a desired site. The device can be configured with a stimulation mode to provide nerve stimulation as described herein. The stimulus location can be one or more of many locations on the ear of the subject as described herein. The stimulus can be delivered to the ear and other locations of the subject as described herein. The device may comprise a user interface, and can include an on/off switch, for example. The user interface can be provided with an app of a mobile device coupled to the wearable device.

The responsiveness of the treatment can be monitored with sensors on the device. In some cases, one or more sensors for detecting responsiveness of treatment are provided onboard the device. Alternatively or additionally, one or more sensors for detecting physiological condition may be located remotely from the device. These sensors may be located on or near the subject body and the collected sensor measurement may be transmitted to the device or a processor in communication with the device.

While the sensors can be configured in many ways, in many embodiments the sensors and associated circuitry are configured to measure and detect atrial fibrillation (AF), bradycardia, tachycardia, heart rate variability (HRV) and other measures of cardiac function, for example. Various types of sensors can be utilized by the device. For example, the device may comprise electrical sensors to measure the electrocardiogram (ECG) signal of the subject. Alternatively or in combination, additional sensors can be provided such as accelerometers to measure movement patterns and orientation of the subject. The device may comprise sensors to measure oxygenation of tissue such as a pulsed oximeter, for example. As described above, the electrical sensors may be located on the device or placed on a location of human body remote from the device.

The device can be configured to automatically provide the dosing of the treatment to the subject, for example with a treatment table/library stored locally on the device. The treatment can be titrated so as to provide a sufficient amount of stimulus to provide therapeutic benefit. The treatment table or library may be local on the device or remotely accessible by the device. In some cases, the treatments stored in the treatment table/library may comprise predetermined parameters such as mechanical vibratory stimulus location, time duration, stimulus pattern, magnitude, frequency, duty cycle of vibration, pitch or tone of the acoustic stimulus, various parameters of the electrical stimulus, or drug delivery. In some cases, the treatment table may also comprise selection of multi-modal or single-modal, a vibration mode (e.g., unilateral vibration mode, bilateral vibration mode) or various others. Such parameters may be adjusted by user via the user worn device or a user computing device, preset by the system, or automatically updated or loaded from a source (e.g., cloud based server). Alternatively or additionally, the amount of treatment can be increased or decreased as needed, in response to real-time feedback. The device or system may automatically adjust dose based on physiometric inputs in substantially real time. The physiometric inputs may be obtained by an analysis of the one or more sensor measurements and/or user manual inputs. A plurality of parameters of the dosing of the treatment may be adjusted until the physiometric inputs reach a pre-programmed setting.

The user worn device can be configured for ease of use, and to provide an acceptable experience to the subject. The device can be configured to play music in combination with therapy, for example. Alternatively or in combination, the device can be configured to provide acoustic vibration therapy that corresponds to a specific pitch (note) or a harmonic of a pitch (note) as described herein, so as to make the acoustic stimulus more acceptable to the subject.

In some cases, the device can be configured with active or passive environmental noise cancellation, which can be beneficial to the subject. The device may be configured to provide noise cancellation of audible and non-audible frequencies of sound.

The device can be in communication with an external computing device such that one or more functions of the device can be controlled via the external computing device. The external computing device may be mobile device (e.g., smartphone, tablet, pager, personal digital assistant (PDA)), a computer (e.g., laptop computer, desktop computer, server, or any other type of device. The external computing device may optionally be portable. The external computing device may be handheld. The external computing device may be a mobile device such as a smart phone or tablet and configured with an application (i.e. app) in order to control the user worn device. The app can be configured to generate user reports for the subject to track therapy and performance, and similar reports can be generated for health care providers. The app may be configured to allow a user to input user data or feedback related to the treatment.

The user worn device may comprise wireless communication circuitry that allows the user worn device to communicate with other devices, such as mobile devices as described herein. The user device can communicate with an app on a watch, smart phone or other mobile device. In some instances, the user worn device may be in communication with other sensors or devices located remotely from the user worn device. The user device can communicate with a remote server, such as a cloud based server, and the user device may comprise a component of a cloud based platform as described herein. The cloud based platform can be configured to provide remote access. In some embodiments, the user worn device can be accessed remotely, for example. The wireless communication circuitry may enable a wireless communication of short range or long range. Examples of wireless communications may include, but are not limited to WiFi, 3G, 4G, LTE, radiofrequency, Bluetooth, infrared, or any other type of communications.

The user worn device can be configured to provide appropriate dosing for the subject. The parameter can be programmed with software or other processor instructions resident on the device, for example. The parameters of the device can be adjusted to provide appropriate treatment. The plurality parameters of dosing can be adjusted may include, for example, mechanical vibratory stimulus location, time duration, stimulus pattern, magnitude, frequency, duty cycle of vibration, various parameters of the electrical stimulus, or drug delivery. The range of parameters can be varied during therapy, and can be within an acceptable range as described herein. The stimulus pattern may comprise a pitch (note) of a harmonic, and can be adjusted during treatment to decrease neuronal and nerve adaptation to the stimulus pattern. The dosing can be titrated so as to be appropriate for the subject, and the titration can be determined based on the subject's response to the therapy. The device can be configured to operate at a point (vibratory frequency and intensity) characterized certain functional responses reflected in prevailing heart rate and heart rate dynamics as well as electrical resistance of skin (skin galvanometry) and or pupil diameter changes provided by the neuronal treatment, for example with a treatment downloaded onto the device.

The user worn device can be configured to perform physiometry on the subject and may comprise appropriate sensors and circuitry as is known to one of ordinary skill in the art to measure one or more of heart rate, heart rate variability, sleep quality, blood oxygen saturation and breathing, for example.

The user worn device can be configured to treat many indications, including but not limited to, cardiovascular disorders such as myocardial Infarction, heart failure, atherosclerosis, neurological disorders such as stroke, alzheimers, inflammation and inflammatory disorders such as arthritis, crohns disease and pain for example.

The user worn device is well suited for combination therapies. The device may comprise electrodes and circuitry for combination therapies with acoustic, mechanical vibratory and electrical auricular stimulation. The device can be configured to provide acoustic or electrical auricular stimulation in combination with a wearable defibrillator, for example, such as the wearable defibrillator vest commercially available from Zoll Medical Corporation. The user worn device can be configured to provide auricular stimulation in combination with implantable ECG electrodes, for example. The user worn device can be combined with drug therapies, for example.

The user worn device can be configured to provide stimulation to both ears, with a similar device placed in a second ear of the subject. The user worn device can be configured to provide combination stimulation to other peripheral locations as described elsewhere herein.

Figure 4A:
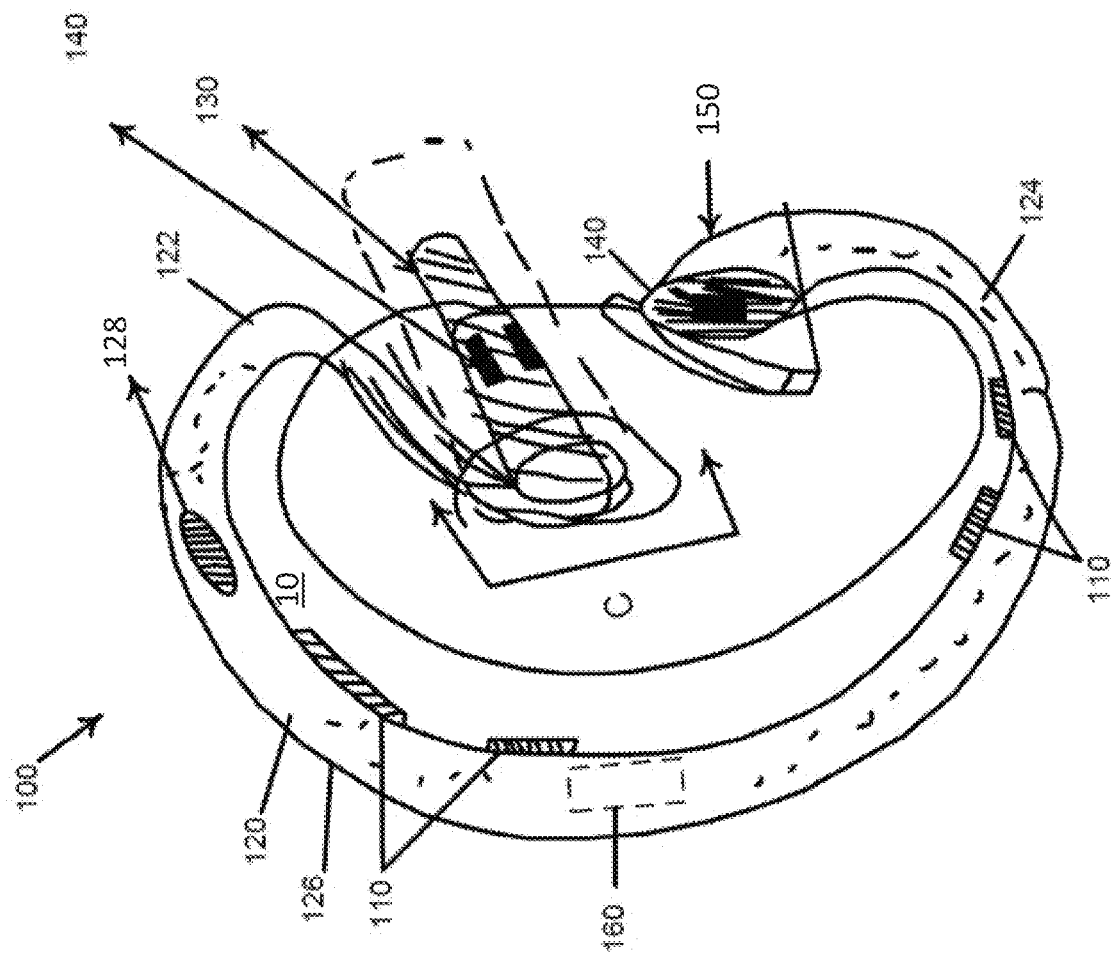
FIG. 4A shows an auricular stimulation device in accordance with some embodiments.

FIG. 4A shows an auricular stimulation device in accordance with some embodiments. The auricular stimulation device 100 is shown positioned on an auricle 10 of an ear. The auricular stimulation device 100 may comprise one or more sensing electrodes 110. The one or more sensing electrodes 110 may be in contact with at least a portion of the auricular location and configured to detect galvanic skin response, heat flow, skin temperature, or a heart rate of a subject. The auricular stimulation device 100 may comprise a support 120 configured to support components of the auricular stimulation device. The auricular stimulation device 100 can be configured for placement on the pinna of the ear. The auricular stimulation device may comprise circuitry 160 coupled to the sensing electrodes.

The auricular stimulation device 100 can be configured in many ways to provide beneficial stimulation to the subject. For example, the auricular stimulation device support 120 can be configured to fit substantially behind an upper portion of the auricle 10 of the subject. The support 120 may comprise an upper extension 122 configured to apportion configured for placement within the ear canal of the subject. The portion configured within the ear canal of the subject may comprise an ear canal portion 130. The ear canal portion 130 can be shaped to the ear canal of the subject, for example with molding as is known to one of ordinary skill in the art. In some cases, the ear canal portion 130 may have a geometry or dimension substantially fit within the external ear canal 20 so as to provide sufficient contact to the skin. A length and/or diameter of the ear canal portion 130 may determine the nerves can be stimulated.

The auricular stimulation device 100 may comprise a behind the ear portion 150 for placement behind a lower portion of the auricle of the subject. The behind the ear portion 150 may comprise an actuator 152 such as a motor configured to induce vibrations on the auricle of the subject. The lower behind the ear portion 150 can be coupled to the support 120 with a lower extension 124 extending from the upper portion of the support to the lower portion 150. Although the behind the ear portion 150 is shown coupled to the upper portion with an extension 124, this extension is optional. Similarly, although the ear canal portion is shown coupled to the behind the ear unit with an extension 122, this extension is also optional. For example, the ear canal portion may comprise power circuitry and communication circuitry configured to communicate with other components such as wireless communication circuitry. The behind the ear portion 150 may also comprise separate power circuitry and communication circuitry to communicate with other components of the system.

The auricle stimulation device 100 can be configured in many ways to beneficially treat a subject. For example, the behind the ear portion, the upper portion, or the ear canal portion may comprise the actuator as described herein in order to stimulate the subject with mechanical vibrations. The actuators may comprise any types of suitable motors such as DC brushless motor or piezoelectric vibration actuators. The actuator can be located in any portion of the auricle stimulation device. For example, the actuator may be located within a housing of the upper behind the ear portion, lower portion behind the ear or within the ear canal. The actuator may actuate a mechanical vibrational movement of the ear canal portion 130 so as to stimulate the sensory nerves within the ear canal. The entire ear canal portion 130 may be actuated to have a vibrational movement such that one or more sensory nerves are stimulated simultaneously. In some instances, the ear canal portion can be actuated selectively such that selected location of the ear canal is stimulated. It should be noted that various other mechanisms can be used to induce vibration such as electronically controlled deformation of piezoelectric materials.

The sensing electrodes 110 can be located on the upper behind the ear portion, the lower portion of the behind the ear portion, or within the ear canal in combinations thereof. The sensing electrodes 110 are configured to measure heart rate of the subject or various other physiometry of the subject as described elsewhere herein. The one or more sensing electrodes may be of the same type or different types. The one or more sensing electrodes may be placed in a specific arrangement in order to measure a physiological condition. For example, a plurality of sensing electrodes may be spaced with the spacing within a range from 2 to 4 centimeters from the first electrode and the second electrode in order to generate a differential signal to measure heart rate of the subject.

The one or more sensing electrodes 110 and/or stimulation electrode 140 are coupled to the circuitry 160. For example, the circuitry 160 can be coupled to the measurement electrodes 110 and/or a stimulation electrode 140 via wired connection. The circuitry 160 may be configured to process measurement collected by the sensing electrodes 110 as well as generate electrical signals to the simulation electrodes 140. The stimulation electrodes 140 can be used in combination with acoustic vibrations to provide a synergistic treatment benefit to the subject and by modulating the type of stimulus in order to decrease adaptation of the central nervous system to the stimulus as described herein. The stimulation electrodes 140 can be located in various locations to contact the skin according to the therapy. The stimulation electrodes 140 can be located at the ear canal portion to contact the skin of the ear canal and/or the lower portion behind the ear or contact the lobe.

Figure 4B:
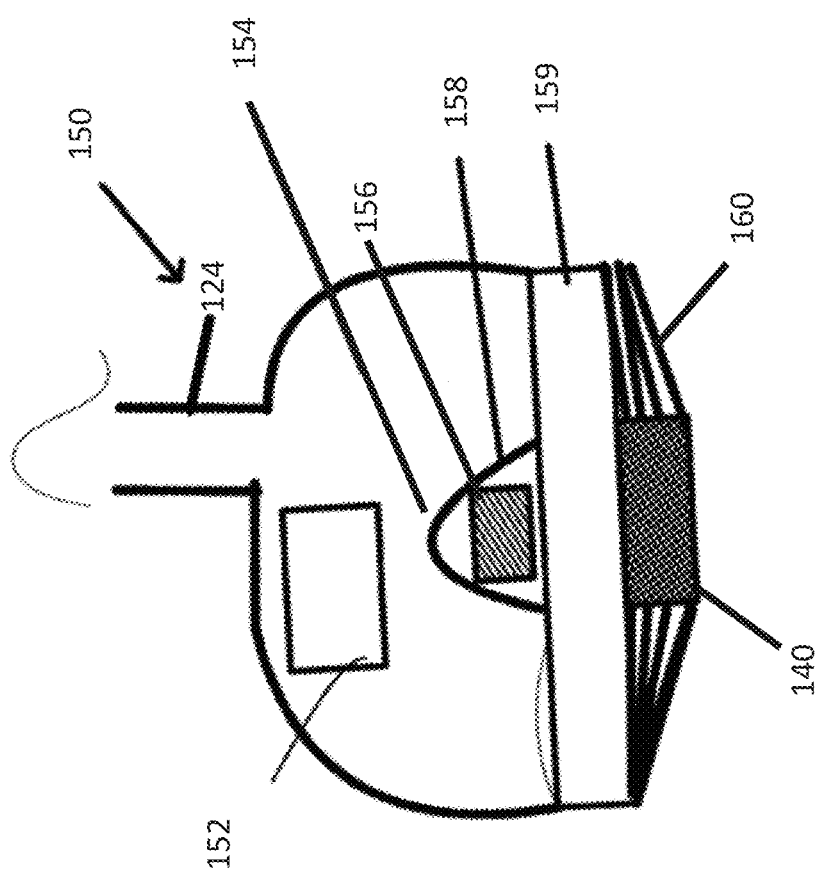
FIG. 4B shows the lower behind the ear portion, in accordance with some embodiments.

FIG. 4B shows the lower behind the ear portion 150 in accordance with some embodiments. The lower behind the ear portion may comprise an electrode or electrodes 140 configured to deliver stimulus to the subject. The lower portion 150 may comprise an actuator 152 as described herein. The actuator 152 may be used alternatively to the stimulation electrodes 140 or in combination with stimulation electrodes 140. The lower portion 150 may comprise an adhesive patch 160. The adhesive patch 160 may comprise an adhesive patch of a removable electrode that can be replaced. The removable portion 159 may comprise the adhesive patch 160 and electrodes 140 in order to allow the portion to be removed and replaced when helpful, for example after use over a period of time such as a day, a week or a few weeks. The removable portion and the lower portion 150 may comprise engagement structures 154 configured to allow removal and replacement of the disposable portion 159. The engagement structures 156 can be configured in many ways and may comprise, for example, a pin in a channel in which the channel is located on the lower portion 150 and sized to receive a pin 156. The channel 158 can be sized to receive the pin 156. For example, the lower portion 150 can be coupled to the circuitry of the upper portion 126 with wires, electrodes, traces and other structures in order to couple to the circuitry 160 to drive the lower portion 150.

Figure 5A:
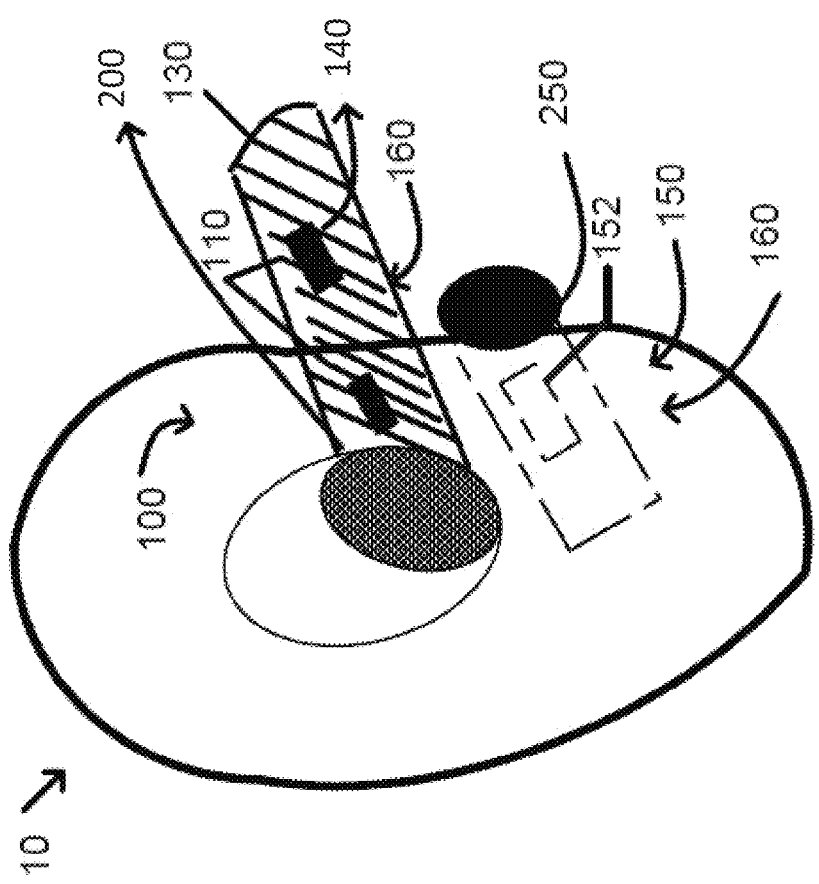
FIG. 5A shows an auricular stimulation device comprising an ear canal portion and a behind the ear portion, in accordance with some embodiments.

FIG. 5A shows an auricular stimulation device comprising an ear canal portion and a behind the ear portion. The lower portion 150 may comprise components as described herein such as electrodes and actuators and circuitry 160. The lower portion 150 may comprise of magnet 250 to couple to the ear canal portion 130. The ear canal portion 130 may comprise components such as sensing electrodes 110 and circuitry 160 as described herein. The ear canal portion 130 can be sized and shaped to fit within the ear canal and may comprise of magnetic material in order to magnetically attract and couple the lower portion to the ear canal portion. The ear canal portion 130 may comprise of electrodes 110. The ear canal portion 130 may comprise sensing electrodes 110 or stimulation electrodes 140 as described herein. The ear canal portion 130 may comprise actuator 152 as described herein. A behind the ear portion 150 may comprise the electrodes, the adhesive and the removable portion as described herein.

Each of the ear canal portion 130 and the lower portion 150 may comprise separate components configured to communicate with wireless communication circuitry and each comprising separate power and processor circuitry as described herein. This is beneficial to provide a device that can adapt to various uses and different users by the modular components of the device. For instance, the ear canal portion 130 or the lower portion 150 can be modular pieces that can be replaced without interfering with other components of the device. In another instance, the ear canal portion with any customized shape can be mated or coupled to the lower portion without affecting the overall function or operations of the device. Alternatively, the user worn device is an integral single piece that the ear canal portion and the lower portion are not separable. In this case, the ear canal portion and the lower portion may share the circuitry, power and various other electronic components.

While the ear portion 200 can be configured in many ways, in some embodiments the ear canal portion comprises a pod 200 sized for placement within the ear canal of the subject. The pod 200 can be configured similarly to the ear canal portion as described herein and may comprise communication circuitry, processor circuitry, electrodes and an actuator as described herein and can be configured to couple to the lower portion 150 with the magnets as described herein. In some embodiments the lower portion 150 and the pod 200 may comprise physically separable components in which the ear canal portion is sized to fit and shape within the ear canal as described herein and the lower portion 150 is configured to couple to the ear, for example with an adhesive as described herein and optionally with magnet 250.

Figure 5B:
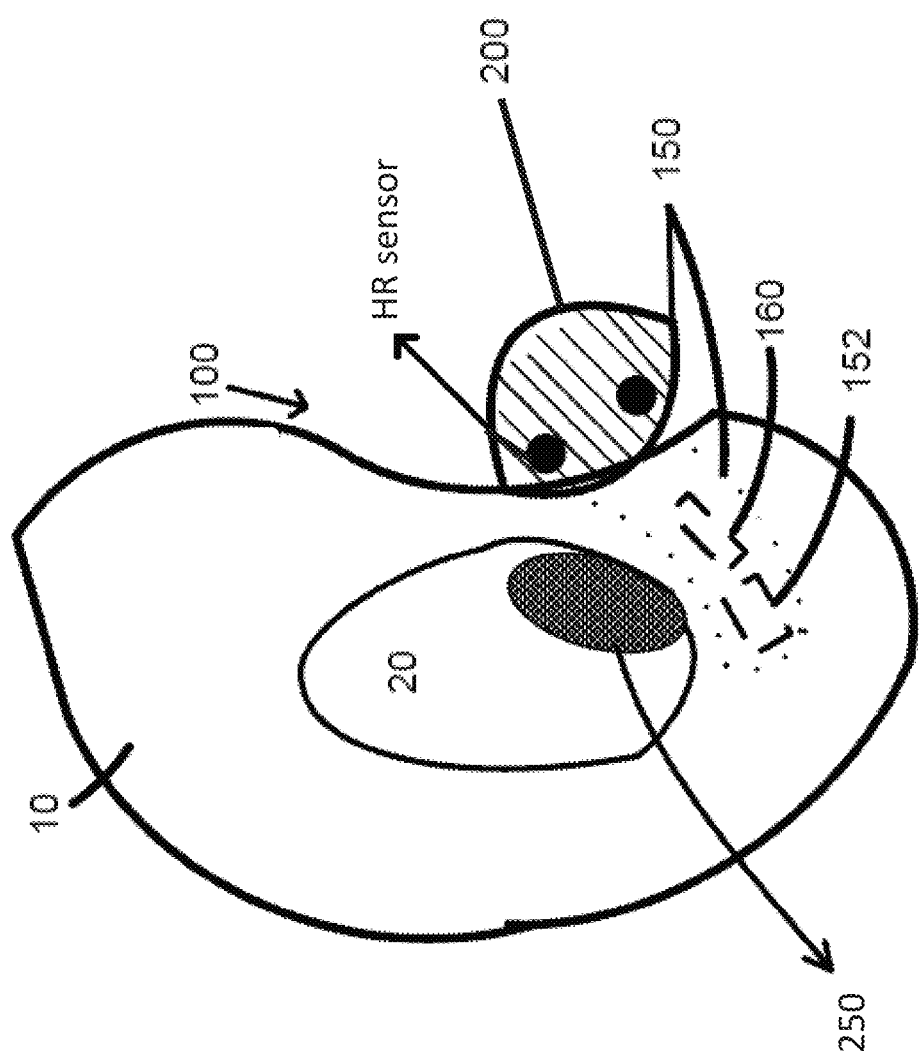
FIG. 5B shows auricular stimulation device in which the behind the ear component comprises a pod, in accordance with some embodiments.

FIG. 5B shows auricular stimulation device 100 in which the behind the ear component 150 comprises pod 200 as described herein. In an example, the pod 200 may comprise the circuitry, the heart rate sensors, the stimulation electrodes and the actuator as described herein. A magnet 250 can be sized and shaped for placement within the ear canal in order to couple the pod 200 to the lower portion of the pin 210 behind the ear. While the magnet 250 can be sized and shaped in many ways, in some embodiments the magnet 250 is typically sized and shaped to fit within the ear canal 20. For example, the magnet 250 may comprise smaller cross sectional dimensions in a cross-sectional size of the ear canal 20.

Figure 6A:
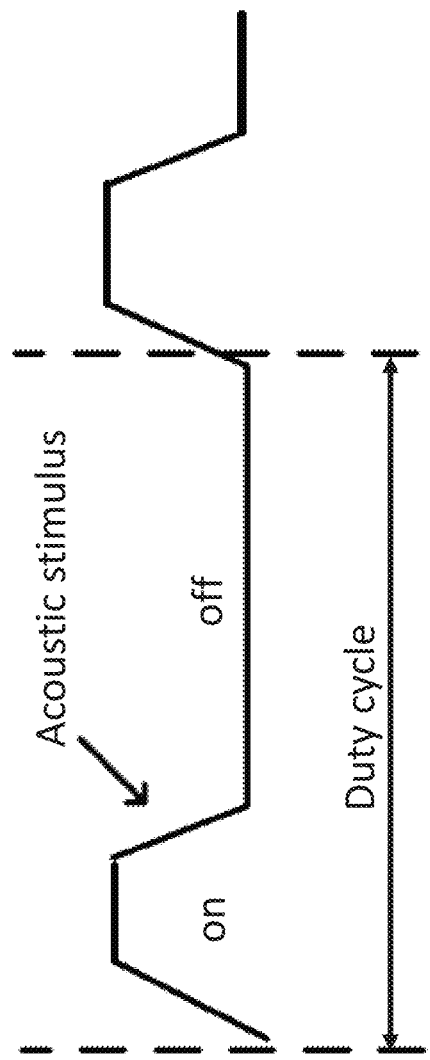
FIG. 6A shows a waveform for acoustic stimulation, in accordance with some embodiments.

FIG. 6A shows a stimulus waveform for controlling the vibratory stimulation in accordance with some embodiments. The stimulus waveform may comprise a ramp up and a ramp down, for example. Alternatively or in combination, the stimulus waveform may comprise an approximately sinusoidal waveform or pulse signals. The stimulus waveform may comprise a voltage and/or current to an actuator, or a current to an electrode, for example.

Figure 6B:
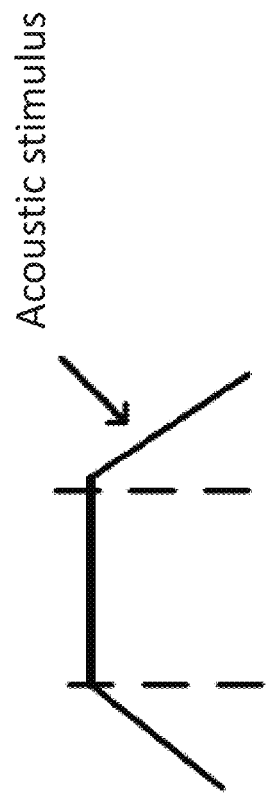
FIG. 6B shows a duty cycle of a waveform as in FIG. 6A.

FIG. 6B shows a duty cycle of the stimulus waveform. In general the duty cycle corresponds to an amount of time the actuator or electrode is active (e.g. on), divided by an amount of time of actuator or electrode is off, for example.

The stimulus wave from may comprise a varying frequency, or a plurality of frequencies, for example. The frequency may be within an audible range such as 20 Hz Hertz to about 20,000 Hertz including at least a frequency corresponding to a harmonic of a pitch (note). Pitches may generally refer to a perceptual ordering of sounds on a frequency-related scale. A particular pitch relates to a position of a single sound in the range or scale. Pitch and tone may be related in that a tone represents the "quality" of a sound, such as how shrill or full an audible pitch sounds. A note is a named pitch. For instance, Western music generally refers to the 440 Hz pitch as "A" (more specifically, A4). In some cases, the acoustic stimulus may comprise harmonic sound characteristics. Harmonic sound characteristics may include multiple sound frequencies, of which higher sound frequencies are approximately integer multiples of a lowest sound frequency (or fundamental frequency). Work in relation to embodiments suggests that varying the waveform can decrease neural adaptation to the stimulus. The stimulus can be varied in many ways, for example the waveform may comprise a plurality of individual waves spaced apart with an amount of time between each pulse. The amount of time may correspond to a frequency of a pitch (note) as described herein.

The frequency of the pitch may correspond to a piano key frequency as is known to one of ordinary skill in the art, for example as described at the Wikipedia website (en.wikipedia.org/wiki/Piano_key_frequencies).

TABLE 2

Piano key notes

| Piano Key | Helmholtz Name | Scientific Name | Frequency (Hz) |
|---|---|---|---|
| 44 | e' | $E_4$ | 329.628 |
| 43 | d♯'/e♭' | $D♯_4/E♭_4$ | 311.127 |
| 42 | d' | $D_4$ | 293.665 |
| 41 | c♯'/d♭' | $C♯_4/D♭_4$ | 277.183 |
| 40 | c' 1-line octave | $C_4$ Middle C | 261.626 |
| 39 | b | $B_3$ | 246.942 |
| 38 | a♯/b♭ | $A♯_4/B♭_3$ | 233.082 |
| 37 | a | $A_3$ | 220.000 |
| 36 | g♯/a♭ | $G♯_3/A♭_3$ | 207.652 |
| 35 | g | $G_3$ | 195.998 |
| 34 | f♯/g♭ | $F♯_3/G♭_3$ | 184.997 |
| 33 | f | $F_3$ | 174.614 |
| 32 | e | $E_3$ | 164.814 |
| 31 | d♯/e♭ | $D♯_3/E♭_3$ | 155.563 |
| 30 | d | $D_3$ | 146.832 |
| 29 | c♯/d♭ | $C♯_3/D♭_3$ | 138.591 |
| 28 | c small octave | $C_3$ | 130.813 |
| 27 | B | $B_2$ | 123.471 |
| 26 | A♯/B♭ | $A♯_2/B♭_2$ | 116.541 |
| 25 | A | $A_2$ | 110.000 |
| 24 | G♯/A♭ | $G♯_2/A♭_2$ | 103.826 |
| 23 | G | $G_2$ | 97.9989 |
| 22 | F♯/G♭ | $F♯_2/G♭_2$ | 92.4986 |
| 21 | F | $F_2$ | 87.3071 |
| 20 | E | $E_2$ | 82.4069 |
| 19 | D♯/E♭ | $D♯_2/E♭_2$ | 77.7817 |
| 18 | D | $D_2$ | 73.4162 |

The stimulus waveform may be the waveform for the mechanical vibratory stimulus. The electrical signals for the electrical stimulus may or may not be synchronized with the mechanical vibratory waveform. As described previously, the device can provide unilateral vibration mode, bilateral vibration mode or a combination of both. When a unilateral vibration mode is selected, the stimulus waveform supplied to the left ear and right ear are synchronized whereas when the bilateral vibration mode is selected, the stimulus waveform supplied to the left ear and right ear are in a rhythmic left-right pattern.

Figure 7:
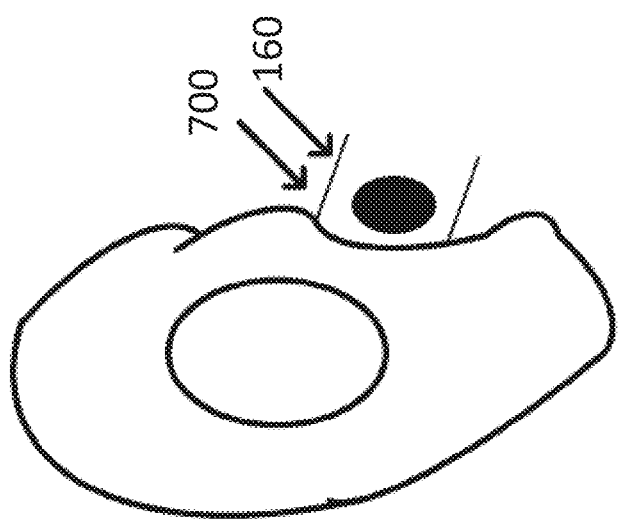
FIG. 7 shows an implantable pellet configured to provide acoustic stimulation, in accordance with some embodiments.

FIG. 7 shows an implantable auricular stimulation device 700. The implantable device 700 may comprise many of the components of device 100 as described herein, including circuitry 160 as described herein. The implantable device 700 may comprise a pellet shaped outer housing comprising a biocompatible material, in order to inject the pellet beneath the skin of the subject. The pellet can be injected into the auricle 10, as described herein. Alternatively or in combination, the pellet can be injected beneath the skin of the ear canal of the subject, for example. The pellet may comprise an active mode for stimulation and a passive mode, for example. The pellet may comprise a housing having dimensions suitable for injection, for example a length of no more than about 10 mm, and width of no more than about 3 mm, for example. The length may be within a range defined by any two of the following values, 2 mm, 3 mm, 4 mm, 5 mm, 6 mm, 7 mm, 8 mm, 9 mm and 10 mm, and the width may be within a range defined by any two of the following values, 0.5 mm, 1 mm, 2 mm, 3 mm, 4 mm, or 5 mm.

Figure 8:
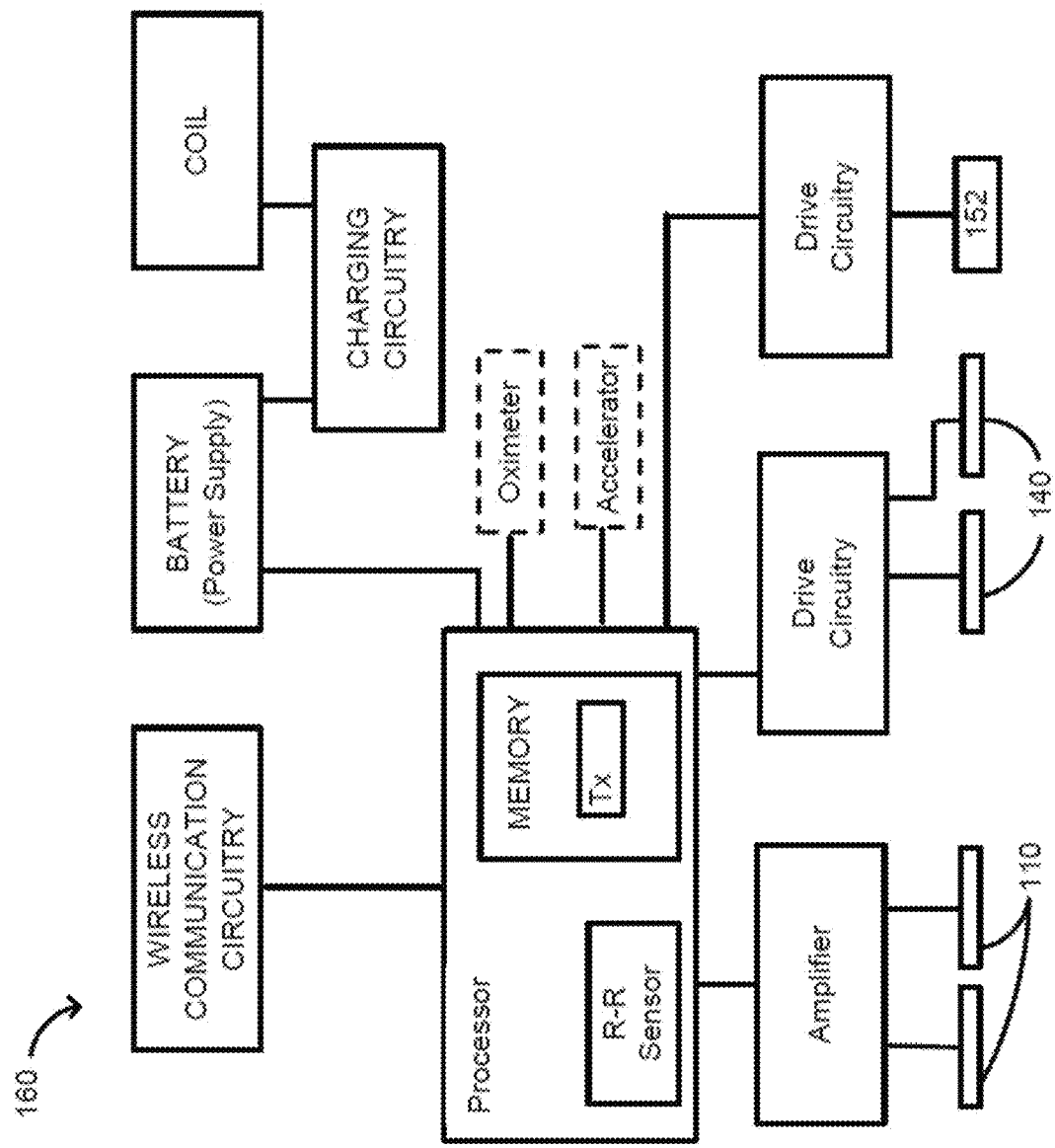
FIG. 8 shows circuitry of the auricular stimulation device to provide auricular stimulation, in accordance with some embodiments.

FIG. 8 shows circuitry of the auricular stimulation device 160, in accordance with some embodiments. The circuitry 160 may comprise a processor, wireless communication circuitry, a power supply (e.g. a battery), an amplifier and drive circuitry. The circuitry 160 optionally comprises charging circuitry coupled to a coil, for example, although the circuitry can be powered and charged in many ways. The wireless communication circuitry may comprise commercially available circuitry such as Bluetooth circuitry, for example. The circuitry 160 may optionally comprise an accelerometer and an oximeter, for example.

The processor may comprise a commercially available processor as is known to one of ordinary skill in the art, and may comprise one or more of many components, such as times, analog to digital converters, digital to analog converters, and memory as described herein. The processor may comprise a gate array, such as a programmable gate array or an application specific integrated circuit, for example. The processor may comprise a memory as described herein. The memory may comprise treatment parameters corresponding to auricular stimulation treatment as described herein. The treatment parameters may comprise parameters of a treatment table with instructions to delivery and vary the auricular stimulation as described herein.

The circuitry 160 can be configured to communicate with a mobile device, such as a smartphone, table or other mobile computing device, for example. The communication circuitry can upload measured data of the subject to a remote cloud based sever, either directly or indirectly through the mobile communication device, for example. The remote server may comprise a database of patient treatments and configured to perform data analytics, e.g. supervised or unsupervised machine learning, in order to determine the appropriate treatment for a given subject based on analytics of a patient population. The treatment parameters can be downloaded from the remote server in response to the subject's reaction to the therapy and demographic data, for example. In some embodiments, the subject can adjust the treatment parameters based on his preferences.

The processor may be coupled to a heart rate (HR) sensor to determine the heart rate of the subject, for example in response to the known R peaks of the heart rate. The processor may comprise instructions to determine the heart rate in response to the amplified electrical signals from sensing electrodes 110.

The circuitry 160 may comprise an appropriate amplifier to amplify electrical signals from the sensing electrodes 110 to determine the heart rate of the subject. The circuitry may be in wired or wireless communication with one or more measurement sensors as described elsewhere herein.

The circuitry 160 may comprise drive circuitry to drive the stimulation electrodes 140 and the actuator 152, for example. The actuator 152 may comprise any actuator known to provide acoustic stimulation as is known to one of ordinary skill in the art. For example, the actuator may comprise an electromagnetic actuator comprising a coil and a magnetic material such as a coil and a rod, a balanced armature transducer, etc. Alternatively or in combination, the actuator may comprise a piezo electric actuator, such as a cantilevered piezo electric transducer, for example.

Although FIG. 6 shows circuitry 160 in accordance with some embodiments, a person of ordinary skill in the art will recognize many adaptations and variations. For example, some of the components may be removed, some of the components duplicated, and the components can be arranged in any order as appropriate. Each of the components of circuitry 160 can be distributed and/or combined in accordance with the present disclosure. For example, the ear canal portion and the behind the ear portion may comprise similar components and/or combinations of circuitry 160.

The circuitry 160 may optionally comprise components for active noise cancelling features. For instance, the circuitry may incorporate a microphone that measures ambient sound, then generate a waveform that is the exact negative of the ambient sound to cancel the noise.

Digital Processing Device

Figure 9:
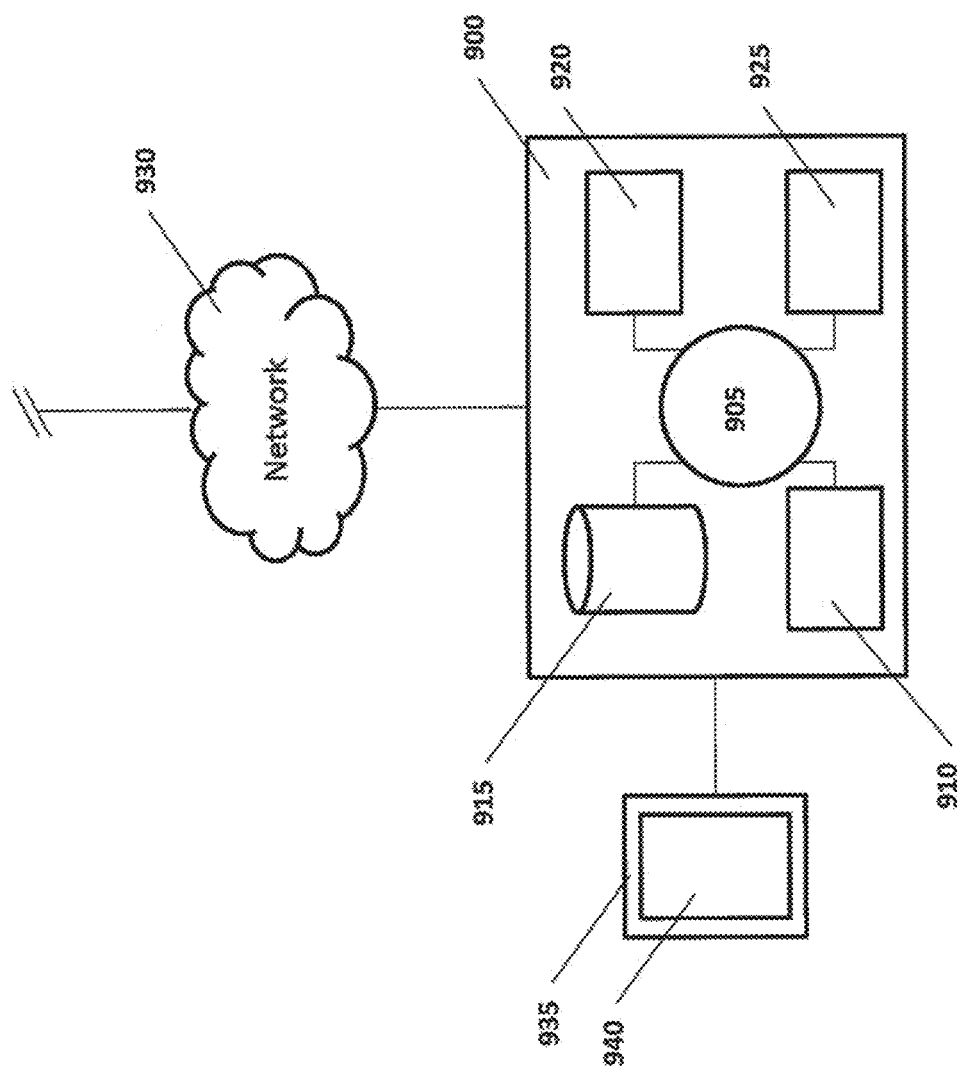
FIG. 9 shows a digital processing device, in accordance with some embodiments.

FIG. 9 shows a digital processing device 900 suitable for use with the circuitry 600 of the auricular stimulation device as described herein. For example, the wireless communication circuitry 600 of the auricular stimulation device can be in communication with digital processing device 900. Alternatively or in combination, the circuitry 600 may comprise one or more components of digital processing device 900. The digital processing device 900 may comprise a display 940 of a mobile device 935, for example. The mobile device 935 may comprise components of digital processing device 900. The mobile device can be configured with a user interface to allow the user to select and/or adjust treatment parameters. The digital processing device may optionally in communication with one or more other sensors placed on a location of the human subject remote to the auricular stimulation device. The digital processing device may process sensor data provided by the remote sensors and/or sensors onboard the auricular device to monitor a response to the therapy.

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3 ®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Referring to FIG. 9, in a particular embodiment, an exemplary digital processing device 900 is programmed or otherwise configured to provide auricular stimulation as described herein. The device 900 can regulate various aspects of the auricular stimulation of the present disclosure, such as, for example, the waveform to be delivered to the auricle of the subject. In this embodiment, the digital processing device 900 includes a central processing unit (CPU, also "processor" and "computer processor" herein) 905, which can be a single core or multi core processor, or a plurality of processors for parallel processing. The digital processing device 900 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines). The storage unit 915 can be a data storage unit (or data repository) for storing data. The digital processing device 900 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the device 900, can implement a peer-to-peer network, which may enable devices coupled to the device 900 to behave as a client or a server.

Continuing to refer to FIG. 9, the CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and write back. The CPU 905 can be part of a circuit, such as an integrated circuit. One or more other components of the device 900 can be included in the circuit. In some cases, the circuit is an application specific integrated circuit (ASIC) or a field programmable gate array (FPGA).

Continuing to refer to FIG. 9, the storage unit 915 can store files, such as drivers, libraries and saved programs. The storage unit 915 can store user data, e.g., user preferences and user programs. The digital processing device 900 in some cases can include one or more additional data storage units that are external, such as located on a remote server that is in communication through an intranet or the Internet.

Continuing to refer to FIG. 9, the digital processing device 900 can communicate with one or more remote computer systems through the network 930. For instance, the device 900 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 900, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, flash memory devices, solid state memory, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of therapy information or user specific information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

The methods and apparatus disclosed are suitable for combination with prior therapeutic approaches. The acoustic auricular stimulation device may comprise one or more electrodes and sensing circuitry to deliver electrical stimulation for therapeutic treatments, as described in U.S. application Ser. No. 11/749,500, filed on May 16, 2007, published as US 2008/0288016, entitled "Systems for Stimulating Neural targets", the entire disclosure of which is incorporated herein by reference.

The auricular stimulation device 100 may comprise one or more actuator components or approaches as described in U.S. application Ser. No. 14/546,784, filed Nov. 18, 2014, published as US 2015/0141879, entitled "Device, System and Method for Reducing Headache Pain", the entire disclosure of which is incorporated herein by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to treat a subject, the apparatus comprising:
    an actuator configured to provide both a vibratory stimulus and an acoustic stimulus to skin of the subject in an area at or near one or more of an auricle or an ear canal of the subject, the area comprising underlying sensory nerve fibers and subcutaneous tissues;
    at least one stimulation electrode to delivery an electrical stimulus to the skin of the subject in the area comprising underlying sensory nerve fibers and subcutaneous tissues; and
    a processor coupled to the actuator and the at least one stimulation electrode, the processor configured with instructions to:
    (i) provide to the subject a stimulation pattern comprising a combination of the vibratory, acoustic, and electrical stimuli to the skin of the subject and the area comprising the underlying subcutaneous tissues and nerve structures at or near the one or more of the auricle or the ear canal, and
    (ii) adjust two or more of the vibratory, acoustic, or electrical stimulation while the stimulation pattern is provided to the skin of the subject.

2. The apparatus of claim 1, wherein the stimulation pattern comprises the vibratory or acoustic stimulus, and wherein the processor is configured with instructions to deliver the vibratory or acoustic stimulus as a plurality of vibratory pulses to the subject, the plurality of pulses comprising a frequency corresponding to a harmonic of a pitch.

3. The apparatus of claim 2, wherein the frequency is within a range from about 20 Hz to about 20,000 Hz.

4. The apparatus of claim 2, wherein the processor is configured to stimulate the ear with a plurality of frequencies corresponding to frequencies of pitch.

5. The apparatus of claim 1, wherein the processor is configured with instructions to provide the acoustic stimulus at a frequency audible to the subject.

6. The apparatus of claim 1, wherein the processor is configured with instructions to automatically deliver the combination of the vibratory, acoustic, and electrical stimuli based on real-time sensor measurements.

7. The apparatus of claim 6, further comprising one or more sensors configured to provide the real-time sensor measurements.

8. The apparatus of claim 7, wherein the one or more sensors comprise one or more of a heart rate sensor, an ECG sensor, an accelerometer, an oxygenation sensor, or a temperature sensor.

9. The apparatus of claim 7, wherein the processor is configured to adjust the two or more of the vibratory, acoustic, or electrical stimulus based on the real-time sensor measurements.

10. The apparatus of claim 9, wherein the two or more of the vibratory, acoustic, or electrical stimulus is adjusted based on real-time feedback from the subject from the real-time sensor measurements.

11. The apparatus of claim 1, wherein the actuator is located in proximity to the at least one electrode in order to stimulate the area with the combination of the vibratory, acoustic, and electrical stimuli.

12. The apparatus of claim 11, wherein the processor is configured to synchronize delivery of the electrical stimulus with delivery of the vibratory stimulus and the acoustic stimulus.

13. The apparatus of claim 1, further comprising drug delivery mechanism configured to release drug in combination with the vibratory, acoustic, and electrical stimuli.

14. The apparatus of claim 1, wherein the apparatus comprises an auricular stimulation device comprising one or more of an ear canal portion or a behind the ear portion.

15. The apparatus of claim 14, wherein the auricular stimulation device comprises the behind the ear portion, and wherein the behind the ear portion comprises one or more sensors configured to provide real-time sensor measurements.

16. A method for treating a subject comprising:
    positioning a first actuator at or near one or more of an auricle or an ear canal of a first ear of the subject to provide both a vibratory stimulus and an acoustic stimulus to skin of the subject at or near the one or more of the auricle or the ear canal of the first ear in a first area comprising underlying sensory nerve fibers and subcutaneous tissues;
    delivering an electrical stimulus to the first ear of the subject using at least one first stimulation electrode;
    generating, with aid of one or more processors, instructions to the first actuator and the at least one first stimulation electrode to provide a stimulation pattern comprising a combination of the vibratory, acoustic, and electrical stimuli to the skin of the subject and the area comprising the underlying subcutaneous tissues and nerve structures at the first ear; and
    adjusting two or more of the vibratory, acoustic, or electrical stimulation while the stimulation pattern is provided to the skin of the subject.

17. The method of claim 16, wherein the instructions comprise delivering the stimulation pattern to the subject, wherein the stimulation pattern comprises the vibratory or acoustic stimulation, and wherein the vibratory or acoustic stimulation is delivered as a plurality of vibratory pulses to the subject, the plurality of pulses comprising a frequency corresponding to a harmonic of a pitch.

18. The method of claim 17, wherein the frequency is within a range from about 20 Hz to about 20,000 Hz.

19. The method of claim 17, wherein the ear is stimulated with a plurality of frequencies corresponding to frequencies of pitch.

20. The method of claim 16, wherein the acoustic stimulus is provided at a frequency audible to the subject.

21. The method of claim 16, wherein the instructions are generated based at least in part on real-time sensor measurements.

22. The method of claim 21, wherein the real-time sensor measurements comprise one or more of a heart rate, a heart rate variability, a measure of sleep quality, an ECG, an accelerometer measurement, a breath rate, an oxygenation percentage, or a temperature.

23. The method of claim 21, wherein the two or more of the vibratory, acoustic, or electrical stimulus is adjusted based on the real-time sensor measurements.

24. The method of claim 23, wherein the two or more of the vibratory, acoustic, or electrical stimulus are adjusted based on real-time feedback from patient from the real-time sensor measurements.

25. The method of claim 16, wherein the actuator is located in proximity to the at least one first electrode in order to stimulate the area with the combination of the vibratory, acoustic, and electrical stimuli.

26. The method of claim 16, wherein delivery of the electrical stimulus is synchronized with delivery of the vibratory stimulus and the acoustic stimulus.

27. The method of claim 16, further comprising delivering drug in combination with the vibratory, acoustic, and electrical stimuli.

28. The method of claim 16, further comprising:
positioning a second actuator at or near one or more of the auricle or the ear canal of a second ear of the subject to provide both the vibratory stimulus and the acoustic stimulus to skin of subject at or near the one or more of the auricle or the ear canal of the second ear in a second area comprising underlying sensory nerve fibers and subcutaneous tissues;
delivering an electrical stimulus to the second ear of the subject using at least one second stimulation electrode; and
generating, with aid of the one or more processors, instructions to the second actuator and the at least one further stimulation electrode to provide a combination of the vibratory, acoustic, and stimulus to the skin and underlying subcutaneous tissues and nerve structures of the subject at the second ear.

29. The method of claim 28, wherein delivery of the combination of the vibratory, acoustic, and electrical stimuli at the first ear is synchronized with delivery of the combination of the vibratory, acoustic, and electrical stimuli at second first ear.

30. The method of claim 16, wherein the combination of the vibratory, acoustic, and electrical stimuli is configured to treat one or more of atrial fibrillation, bradycardia, tachycardia, pain, myocardial infarction, stroke, inflammation, heart failure, atherosclerosis, Alzheimer's disease, arthritis, Crohn's disease, or insomnia.

31. The method of claim 16, wherein the adjusting of the two or more of the vibratory, acoustic, or electrical stimulation decreases a neural adaptation of the subject to the stimulation pattern.

32. The method of claim 16, wherein the adjusting of the two or more of the vibratory, acoustic, or electrical stimulation is based on a response of the subject to the stimulation pattern.

33. The method of claim 16, further comprising cancelling environmental noise with one or more of the vibratory stimulus or acoustic stimulus provided by the first actuator.

34. The apparatus of claim 1, wherein adjusting of the two or more of the vibratory, acoustic, or electrical stimulation decreases a neural adaptation of the subject to the stimulation pattern.

35. The apparatus of claim 1, wherein adjusting of the two or more of the vibratory, acoustic, or electrical stimulation is based on a response of the subject to the stimulation pattern.

36. The apparatus of claim 1, wherein the processor is further configured with instructions to cancel environmental noise with one or more of the vibratory stimulus or acoustic stimulus provided by the actuator.

* * * * *